(12) United States Patent
Patzke

(10) Patent No.: US 6,773,923 B2
(45) Date of Patent: Aug. 10, 2004

(54) INDUCED AGGREGATION AND AGGLUTINATION OF PLATELETS

(75) Inventor: Jürgen Patzke, Marburg (DE)

(73) Assignee: Dade Behring Marburg GmbH, Marburg (DE)

( * ) Notice: Subject to any disclaimer, the term of this patent is extended or adjusted under 35 U.S.C. 154(b) by 428 days.

(21) Appl. No.: 09/809,062

(22) Filed: Mar. 16, 2001

(65) Prior Publication Data

US 2001/0024803 A1 Sep. 27, 2001

(30) Foreign Application Priority Data

Mar. 17, 2000 (DE) ........................................ 100 13 377

(51) Int. Cl.$^7$ .............................................. G01N 33/86
(52) U.S. Cl. ...................... 436/69; 435/13; 73/64.41; 73/64.42; 73/64.43; 600/369
(58) Field of Search ................ 436/63, 69; 422/73; 435/13, 40.5; 73/64.41, 64.42, 64.43; 600/369

(56) References Cited

U.S. PATENT DOCUMENTS

| | | | |
|---|---|---|---|
| 3,694,161 A | * 9/1972 | Kleszynski et al. | 436/70 |
| 4,788,139 A | 11/1988 | Ryan | 435/13 |
| 5,246,832 A | 9/1993 | Michelson et al. | 435/7.2 |
| 5,325,295 A | * 6/1994 | Fratantoni et al. | 356/427 |
| 5,569,590 A | 10/1996 | Speck | 435/13 |
| 5,637,452 A | 6/1997 | Speck | 435/4 |
| 5,854,005 A | 12/1998 | Coller | 435/7.21 |

FOREIGN PATENT DOCUMENTS

DE 33 34 170 A1 3/1984

OTHER PUBLICATIONS

O'Brien, J.R., "Platelet Aggregation", J. Clin. Path., 75:452–455 (1962).

Born, G.V.R. et al., "The Aggregation of Blood Platelets", J. Physiol., 168:178–195 (1963).

Yardumian, Da, et al., "Laboratory Investigation of Platelet Function: A Review of Methodology", J. Clin. Pathol., 39:701–712 (1986).

Longmire, K. et al., "Long–range Interactions in Mammalian Platelet Aggregation", Biophys. J., 58:299–307 (1990).

Bick, R. L., "Laboratory Evaluation of Platelet Dysfunction", Clinics in Laboratory Medicine, 15(1):1–38 (1995).

Schreiner, W. et al., "Computerized Acquisition and Evaluation of Whole Blood Aggregometry Data", Comput. Biol. Med. 21(6):435–441 (1991).

Weiss, H. J. et al., "Quantitative Assay of a Plasma Factor Deficient in von Willebrand's Disease that is Necessary for Platelet Aggregation", J. Clin. Invest., 52:2708–2716 (1973).

Tohgi, H. et al., "Development of Large Platelet Aggregates from Small Aggregates as Determined by Laser–light Scattering: Effects of Aggregant Concentration and Antiplatelet Medication", Thromb. Haemost., 75(5):838–843 (1996).

Kitek, A. et al., "Optical Density Variations and Microscopic Observations in the Evaluation of Platelet Shape Change and Microaggregate Formation", Thromb. Haemost., 44(3):754–758 (1980).

Y. Minamoto, et al. "Detection of Platelet Adhesion/Aggregation to Immobilized Ligands on Microbeads by an Aggregometer" Thrombosis and Haemostasis 76(6):1072–1079 (1996).

English Language Derwent Abstract for DE 33 34 170 A1.

* cited by examiner

*Primary Examiner*—Maureen M. Wallenhorst
(74) *Attorney, Agent, or Firm*—Finnegan, Henderson, Farabow, Garrett and Dunner, L.L.P.

(57) ABSTRACT

The invention relates to a method for measuring the aggregation or agglutination of platelets, where a reaction mixture is mixed in a first reaction phase, and is mixed less vigorously or not at all in a second reaction phase following the first, and the measurement is preferably carried out in the second reaction phase.

41 Claims, 11 Drawing Sheets

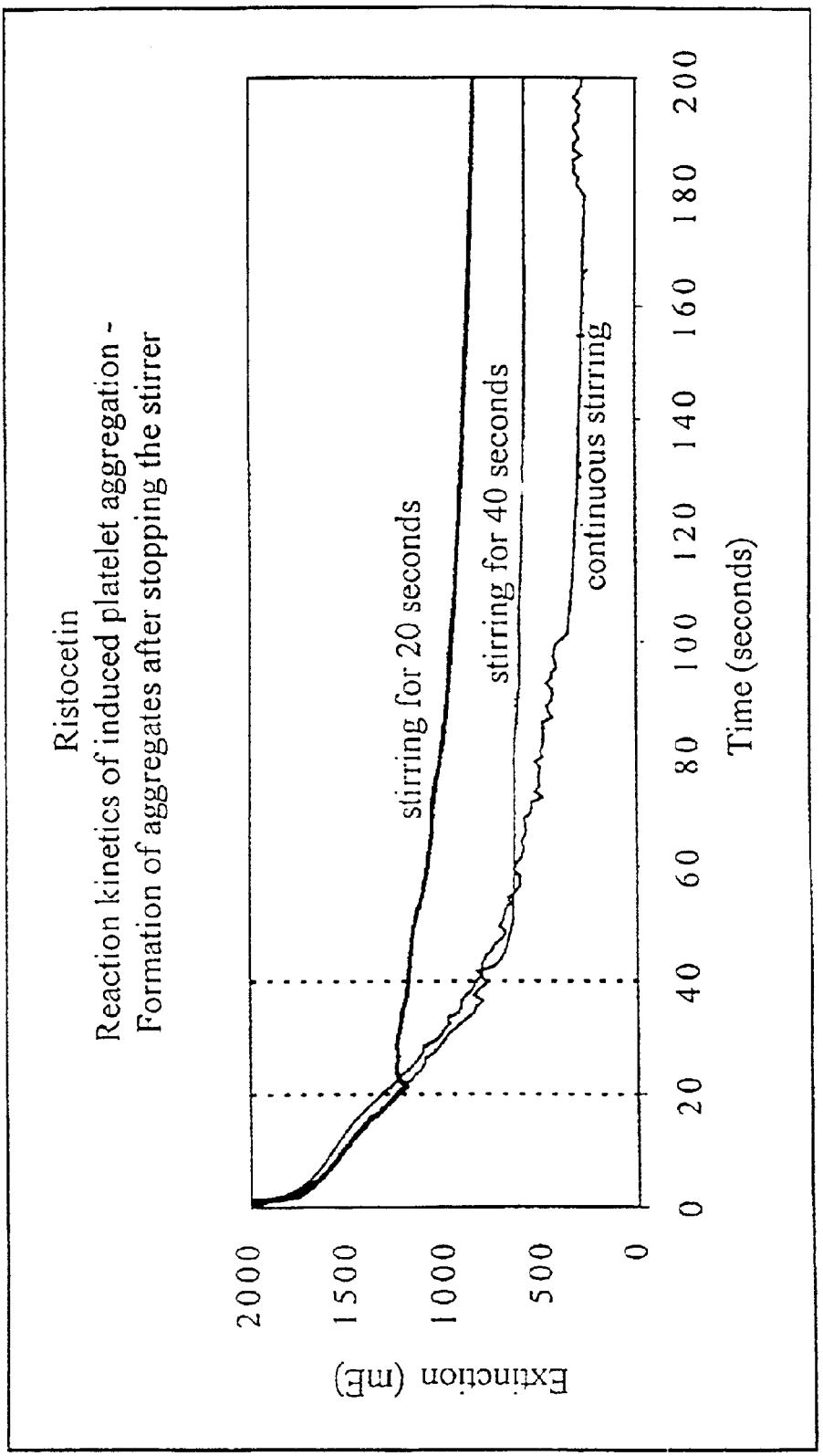

INDUCED AGGREGATION AND AGGLUTINATION OF PLATELETS

The invention relates to a method for measuring the aggregation or agglutination of platelets, where a reaction mixture is mixed in a first reaction phase, and is mixed less vigorously or not at all in a second reaction phase following the first, and the measurement is preferably carried out in the second reaction phase.

Blood consists essentially of the blood plasma, a solution of low molecular weight substances and proteins, and cellular constituents, of which the erythrocytes (red blood corpuscles), leukocytes (white blood corpuscles) and platelets (thrombocytes) account for the largest proportion.

Platelets have the main function in vivo of responding rapidly to an injury and initiating the first steps in wound closure. They are activated by various factors and become during the course of activation "sticky", as it has appropriately been called. They then adhere both to injured surfaces and to one another. The adhesion to one another is called aggregation when it takes place actively, and agglutination when it proceeds passively, that is to say without physiological activity.

Hereinafter and, in particular, also in the claims, on use of the term "aggregation" both aggregation and agglutination of platelets is meant.

The ability to aggregate is thus important for wound closure. It can be enhanced or diminished by a large number of factors. These include, for example, diseases, operations, intake of medicines and the number of platelets. An enhancement of the tendency to aggregate may lead to thromboses and a diminishment in the tendency to aggregate may lead to hemorrhages.

In order to investigate the aggregation properties of platelets, O'Brian (J. Clin. Path., 1962, 15, 452–455) and Born (J. Physiol., 1963, 168, 178–195) developed a method for measuring platelet aggregation which has become widely used in clinical diagnosis in the subsequent decades (Bick R. L., Clinics in Laboratory Medicine, Thrombosis and Hemostasis for the clinical laboratory: Part II, Volume 15, 1, 1–38). For the method, initially platelet-rich plasma is produced. An activator is usually added to the mixture, and the extinction is followed while stirring continuously. The formation of aggregates can be followed quantitatively through the decrease in the extinction. Special instruments, called aggregometers, are used for the measurement, because conventional photometers do not have a controlled stirring mechanism and appropriate modes of evaluation.

The advantage of the method is that the aggregation is measured quantitatively and kinetically, and automation is possible relatively easily. A disadvantage is that specialized instruments with a stirring mechanism during the measurement are required. These instruments, the aggregometers, are costly and acquisition is not worthwhile for every laboratory. Since the number of measurements is often limited, no completely automated instruments have become widely used, and operation is correspondingly inconvenient. On the other hand, a large number of automatic analyzers with a very high degree of automation exist and could in principle, because of the photometric measurement unit, measure the decrease in extinction, but do not have the necessary continuous stirring option.

According to the current state of the art, continuous stirring is necessary for measuring platelet aggregation. As the study by Born (1963) has already shown, the rate of aggregation depends greatly on the stirring rate. More recent review articles on the method assume that the need for stirring is self-evident (Yardumian D. A., J. Clin. Pathol, 39, 1986, 701–712. Bick R. L., Thrombosis and Hemostasis for the Clinical Laboratory: Part II, 15, 1995, 1–38).

The stirring brings about, presumably through an increase in the frequency of collisions, the formation of larger aggregates, called macroaggregates. Macroaggregates are aggregates of platelets which lead to a fall in the extinction in the aggregometer. They are distinctly larger than microaggregates, whose formation is indicated either by no change in the extinction or even by an increase in the extinction (Kitek A. and Bredding K., 1980, Thromb & Haemost, 44, 1980, 3, 154–158). Microaggregates consisting of 2–3 platelets arise even without stirring (Longmire K. and Frojmovic M., Biophys. J, 1990, 58(2): 299–307). However, these microaggregates cannot be seen in conventional aggregometers (Toghi et al., Thromb Haemost, 1996, 75(5): 38–43).

The formation of macroaggregates also proceeds very similarly in the von Willebrand ristocetin cofactor test as in the aggregation of platelets in fresh platelet-rich plasma. In the ristocetin cofactor test, fixed platelets are induced to agglutinate by addition of plasma which contains von Willebrand protein, and ristocetin (Weiss H. J. et al., J. Clin. Invest., 1973, 52, 2708–2716). The turbidimetric measurement with stirring in the ristocetin cofactor test also shows mainly the formation of macroaggregates (Kitek A. and Breddin K., 1980, Thromb & Haemost, 44, 1980, 3, 154–158. Toghi et al., Thromb Haemost, 1996, 75(5): 38–43).

The present invention was thus based on the object of finding a method of measurement with which it is possible to measure platelet aggregation even without continuous stirring.

This object is achieved by the method of the invention for measuring the aggregation of blood platelets (platelets), where a reaction mixture of platelets, preferably physiologically active platelets or fixed platelets, is mixed with other test mixture components in a first reaction phase, and is mixed less vigorously or not at all in a second reaction phase following the first. The platelet aggregation or agglutination is preferably measured in the second reaction phase. Further preferred embodiments of the invention are described in detail in claims 2–17.

It has been found, surprisingly, that the formation of macroaggregates does not necessarily require continuous stirring; on the contrary a short stirring time after addition of the platelet activator is sufficient to induce formation of macroaggregates. The formation of the macroaggregates takes place after the induction phase solely by the action of Brownian diffusion.

Determination of the platelet aggregation induced by various agonists.

FIG. 2)

Determination of the von Willebrand ristocetin cofactor activity after a stirring time of 200 sec.

FIG. 3)

Determination of the von Willebrand ristocetin cofactor activity after a stirring time of 30 sec.

FIG. 4)

Determination of the von Willebrand ristocetin cofactor activity of standard human plasma dilutions after a stirring time of 30 sec.

FIG. 5)

Determination of the von Willebrand ristocetin cofactor activity after a stirring time of 5–60 sec.

FIG. 6)

Establishment of calibration plots with standard human plasma dilutions after a stirring time of 5–60 sec.

FIG. 7a)

Determination of the ADP concentration dependence of platelet aggregation with and without continuous stirring.

FIG. 7b)

Determination of the loss of activity through storage of platelet-rich plasma at room temperature by measuring the aggregation with ADP as agonist with and without continuous stirring.

Figure 1:
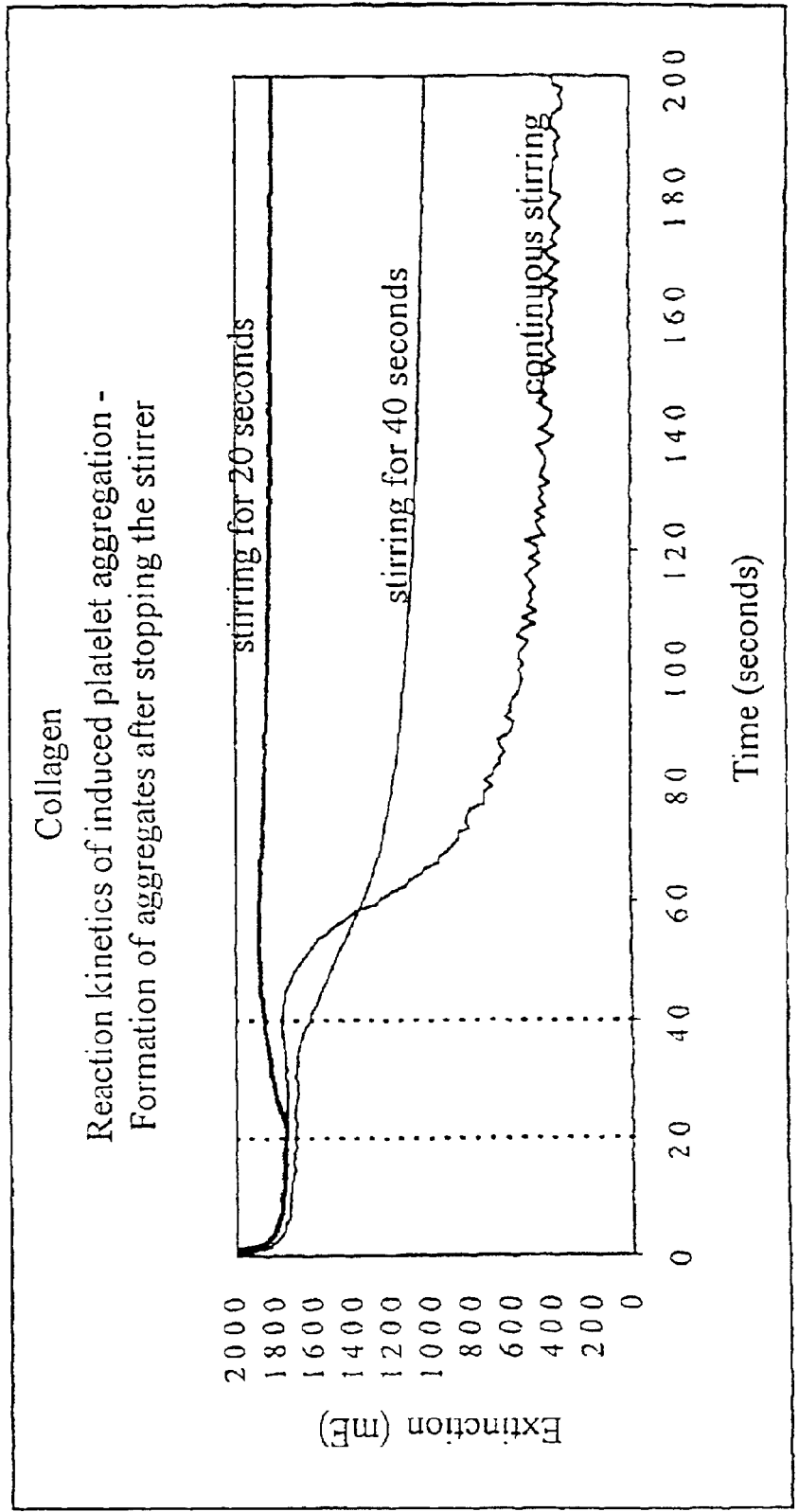
FIGS. 1a–e)
Figure 1:
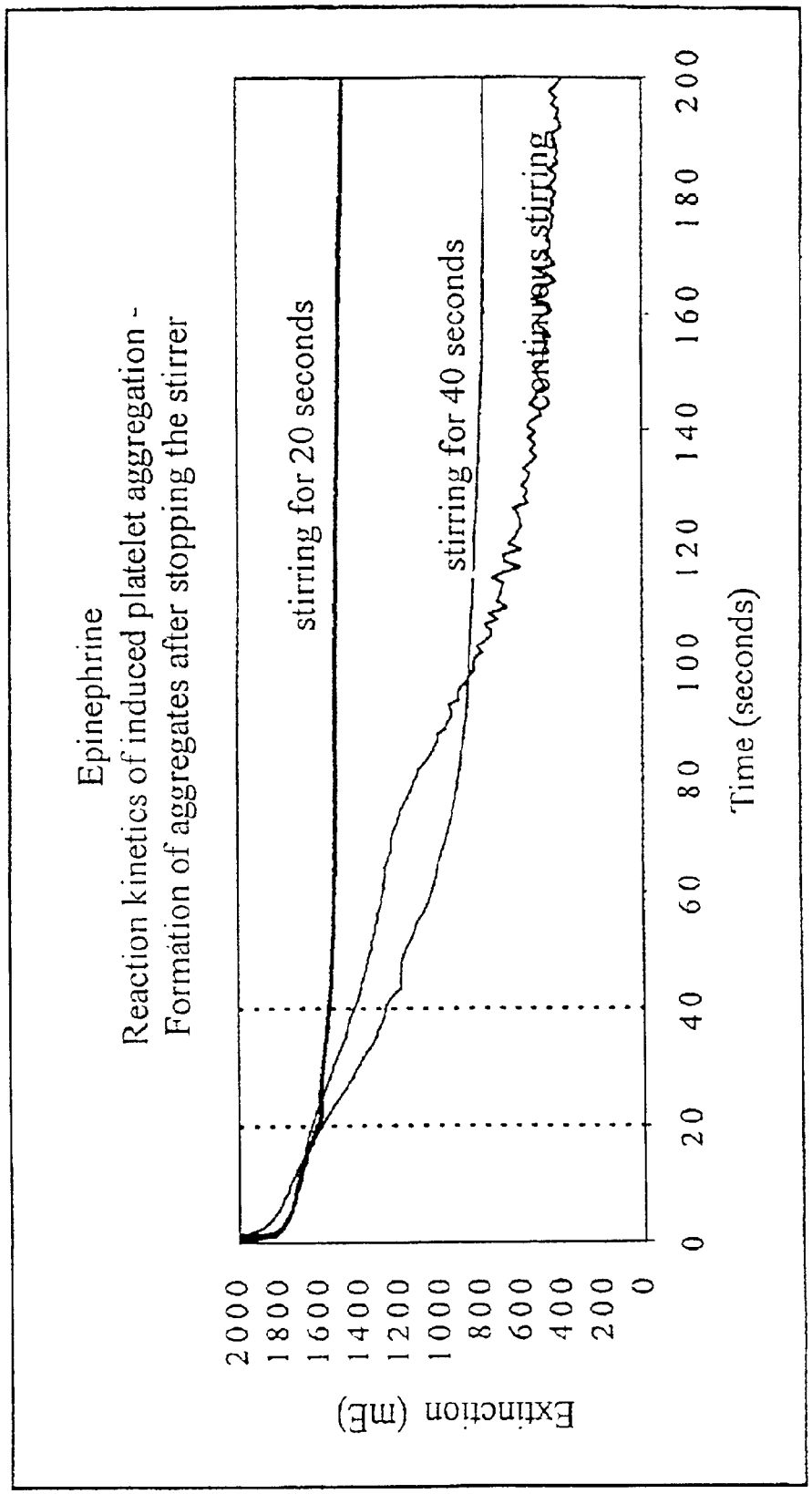
Figure 1:
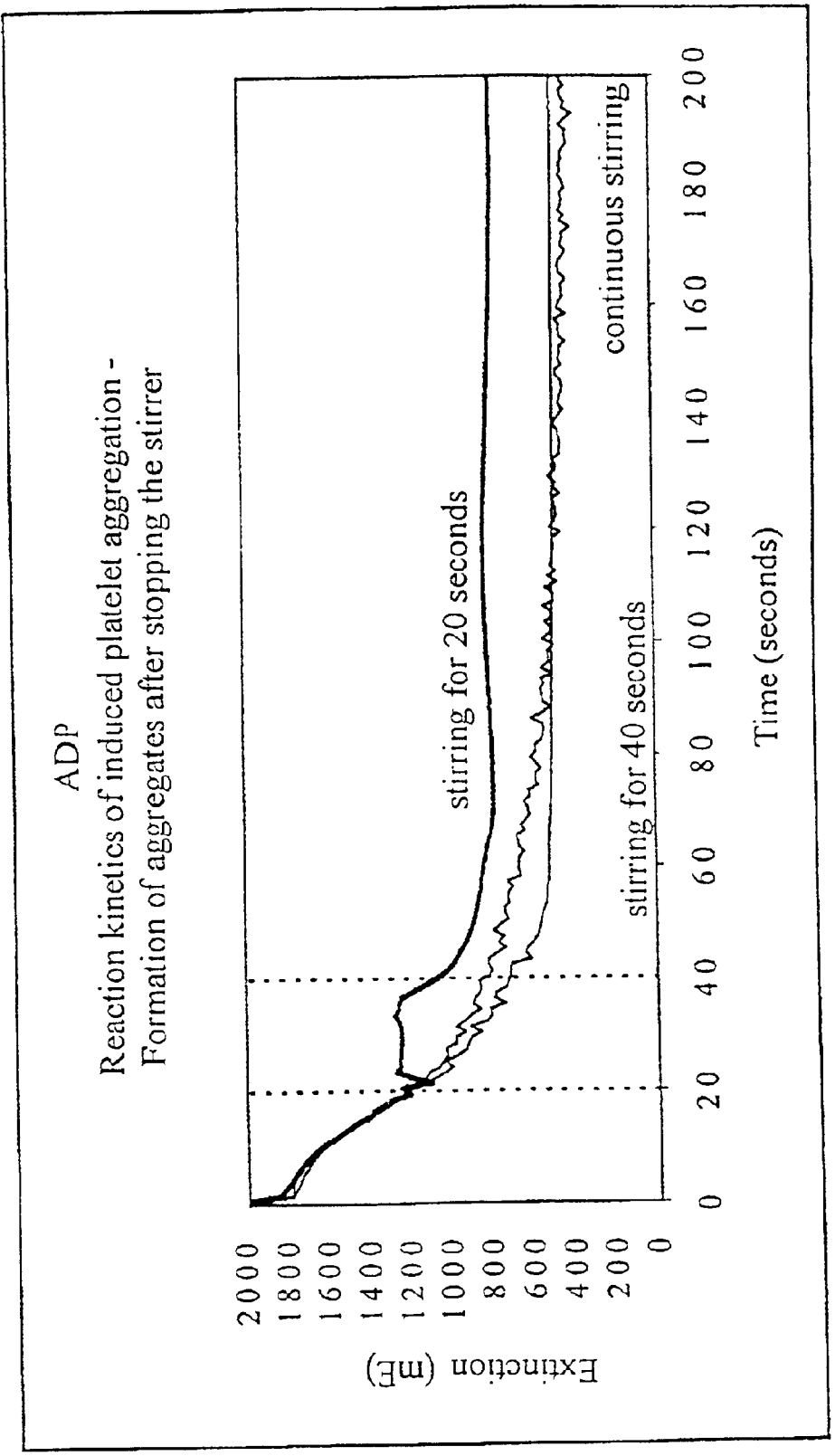
Figure 1:
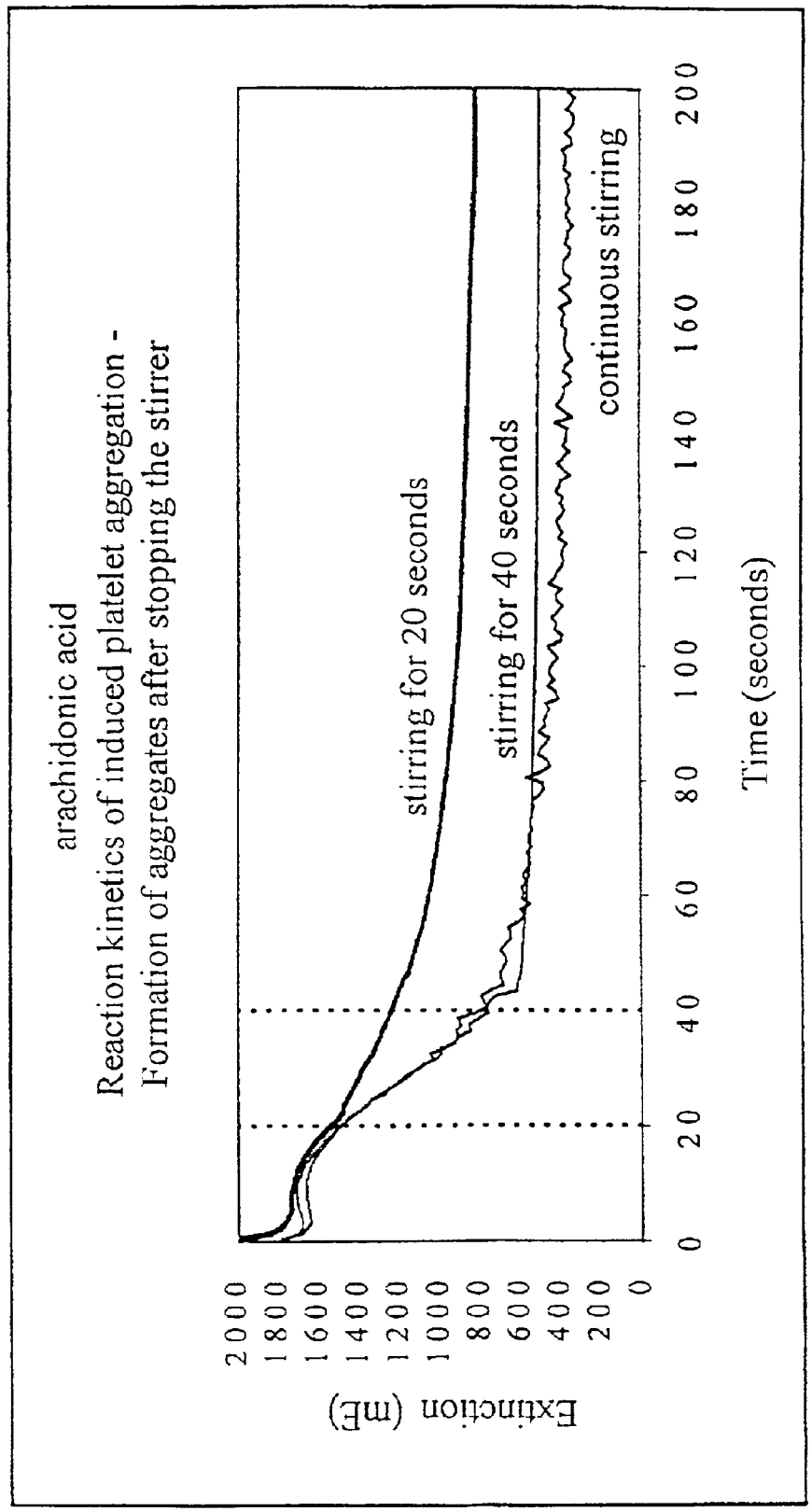

Induction of macroaggregate formation is possible on use of various activators (FIG. 1). Such activators, such as, for example, ristocetin, collagen, ADP or epinephrine, are sufficiently well known to the person skilled in the area of platelet aggregation. A summary of the mode of functioning of various activators and their receptors is to be found, for example, in Blockmans D. et al., Blood Review, 9, 1995, 143–156. The reaction kinetics of the formation of macroaggregates through Brownian diffusion vary widely for different activators. On the one hand, the frequency of collisions of microaggregates with other microaggregates or single platelets is crucial for macroaggregate formation. On the other hand, it is important that a collision is "successful", a part being played in turn by the state of activation, the charge condition, the size and number of the pseudopodia and many other parameters. Since the progress of activation brought about by the activators, also called agonists hereinafter, varies widely, it is understandable why in particular the result of macroaggregate formation varies widely, after stopping the stirrer, with the various agonists. The state or activation at the instant when the stirring is stopped is certainly an important parameter for the extent of the reaction proceeding thereafter.

Figure 7:
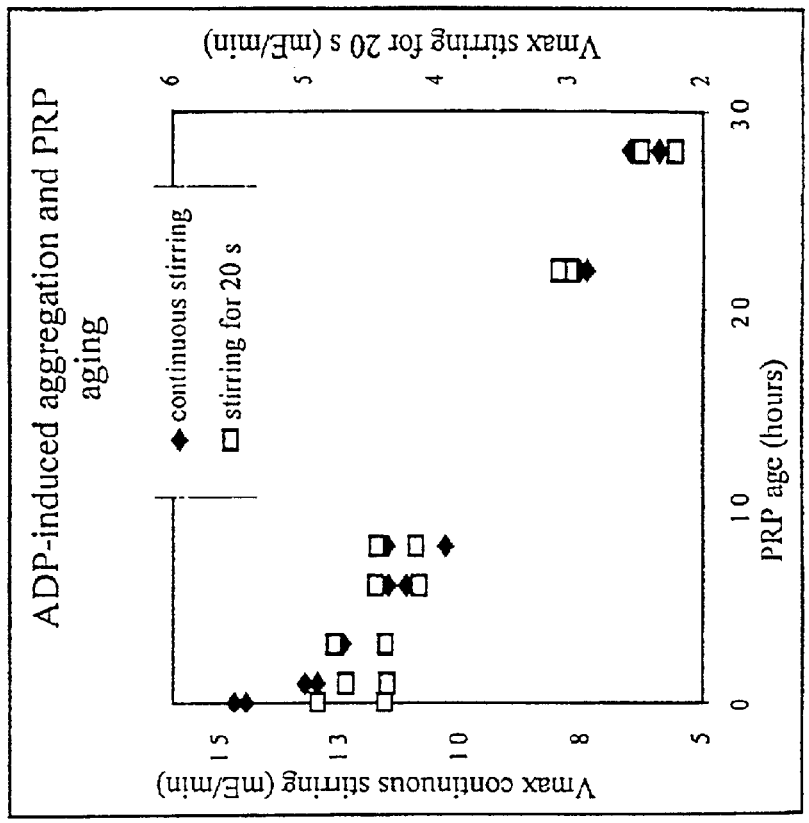
Figure 7A:
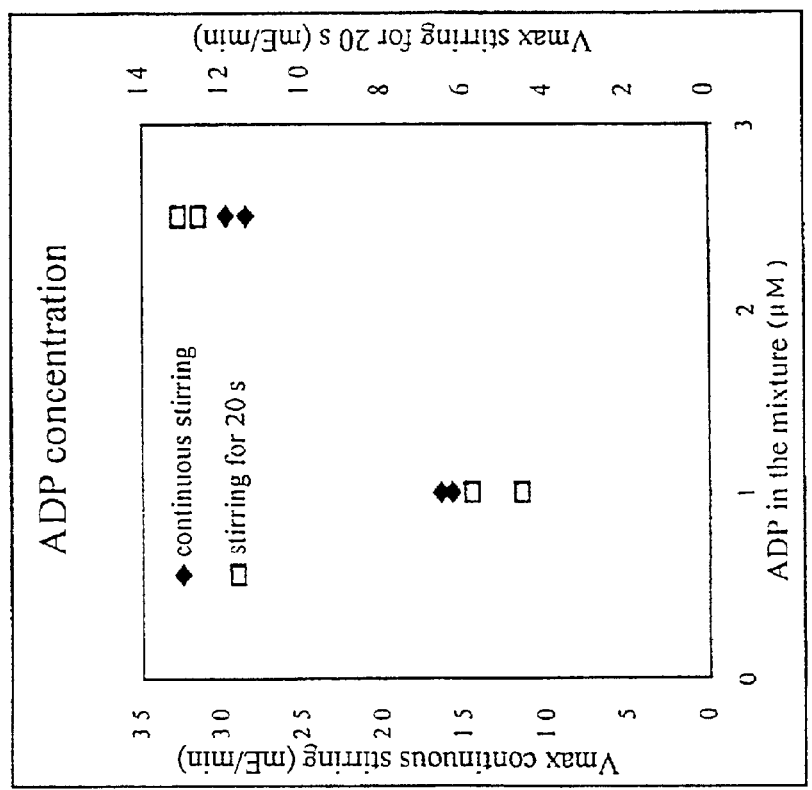

The conventional measurement of aggregation (continuous stirring) and the induced measurement of aggregation (stirring only at the start) are both suitable for measuring the activity of platelets. For this purpose, for example, both the concentration-dependence of the agonist and the aging of platelet-rich plasma have been investigated. The rate of aggregation is at a lower level without continuous stirring. However, it shows a very similar response to a change in concentration of the agonist ADP and to aging of platelet-rich plasma (at room temperature) (FIG. 7).

Figure 2:
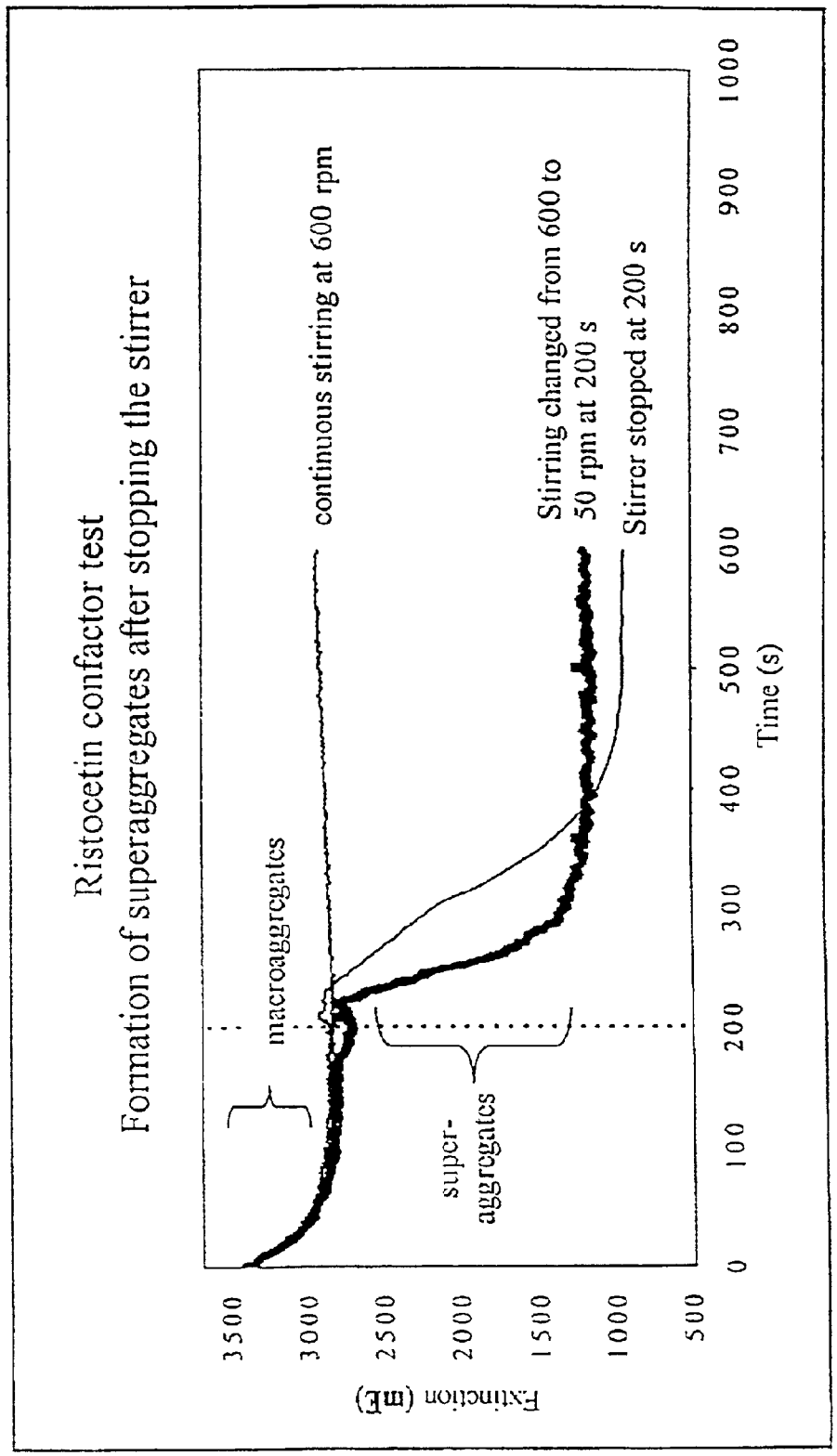

It has also been found, surprisingly, that the stirring not only makes the formation of macroaggregates possible but may also be responsible for the opposite reaction, the destruction of macroaggregates. The apparent end of an aggregation reaction, typically after 5–10 minutes, may in reality be a state of equilibrium between formation and destruction of macro-aggregates. This becomes clear when the stirring is stopped after completion of a large part of the reaction in a typical vWF:RCo (von Willebrand ristocetin cofactor) test. A short time later there is a large fall in extinction, indicating the formation of particularly large macroaggregates, which will be called superaggregates hereafter (FIG. 2). The fall in extinction is about as large as on stirring very gently at 50 rpm (revolutions per minute), which makes it clear that the fall in extinction is not, for example, brought about by sedimentation of aggregates. Since the platelets in the vWF:RCo test are formalin-fixed, it is also precluded that a biochemical reaction starting after a delay brings about the aggregate formation.

In connection with the present invention, stirring also means the other methods known to the skilled worker for mixing liquids, such as, for example, mixing by stirring, shaking, ultrasound or vibration. The mixing can also be effected by agitation in a centrifugal analyzer or by circulating the reaction mixture by pumping through a pipettor or forced addition of the reagents into the reaction vessel.

The stirring rate preferred in the method of the invention is between 200 and 2000 rpm, particularly preferably between 400 and 1200 rpm and very particularly preferably between 400 and 800 rpm.

Figure 3:
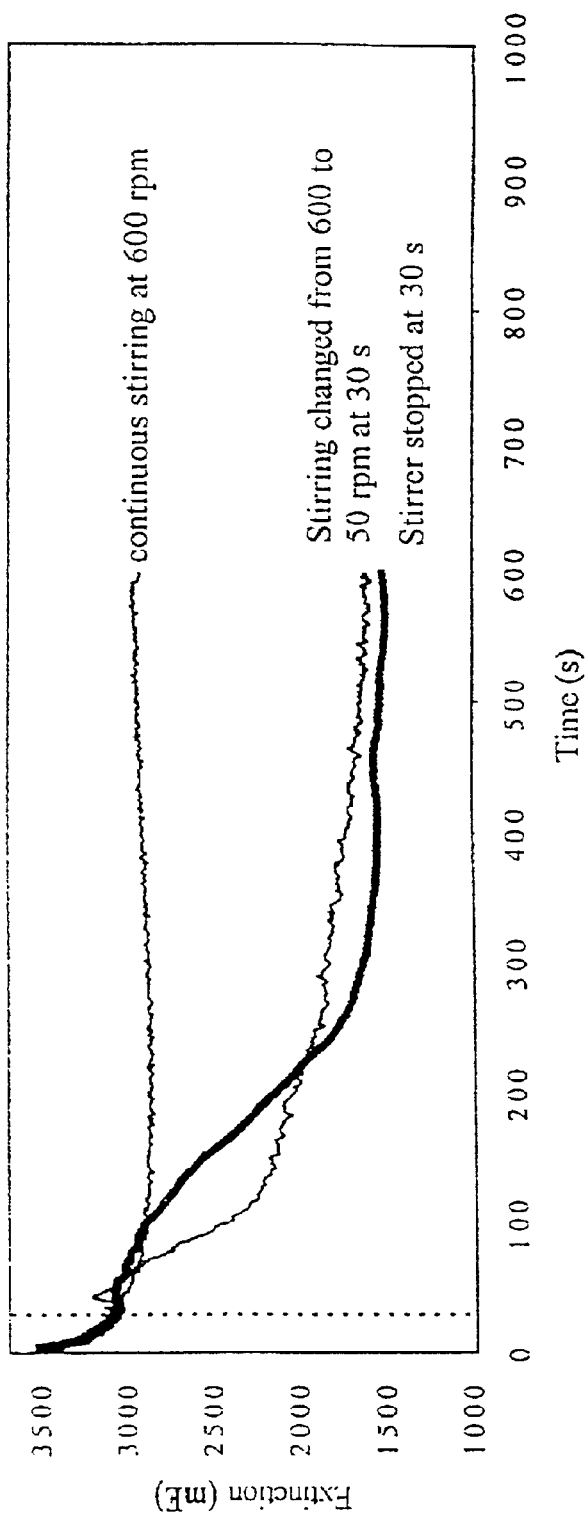

Formation of the superaggregates is induced after only a relatively short time (for example 30 seconds) (FIG. 3).

Figure 4:
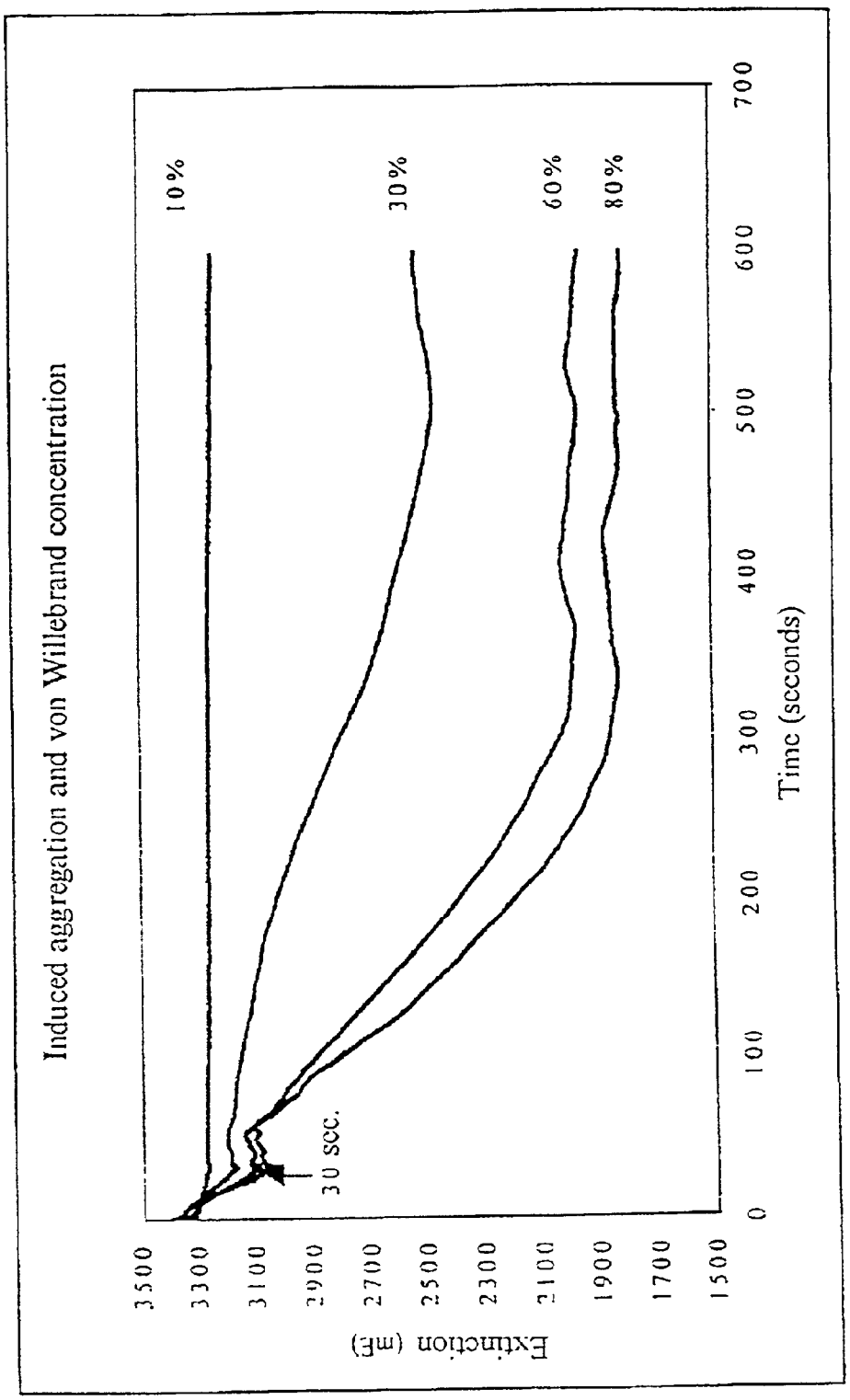
Figure 5:
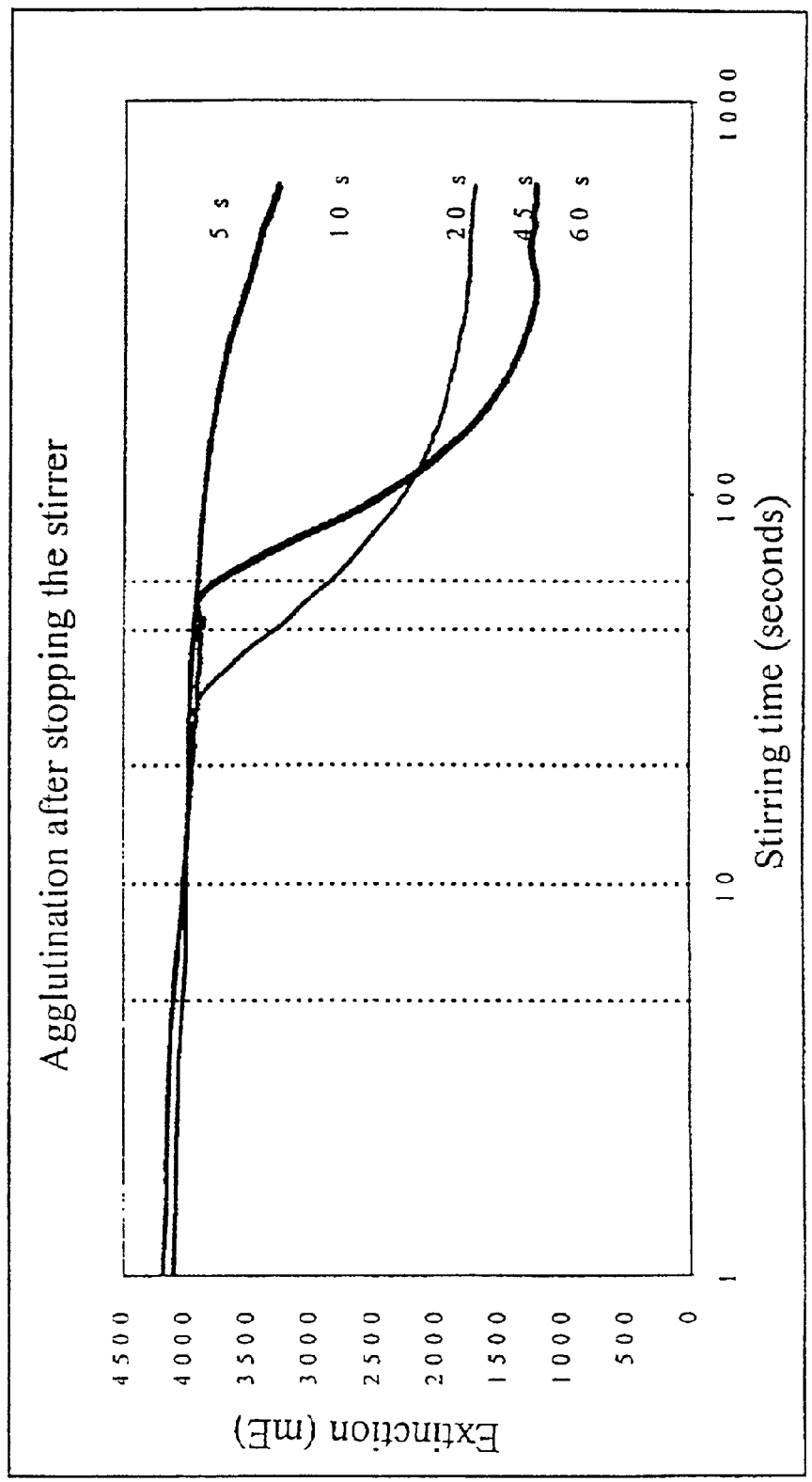
Figure 6:
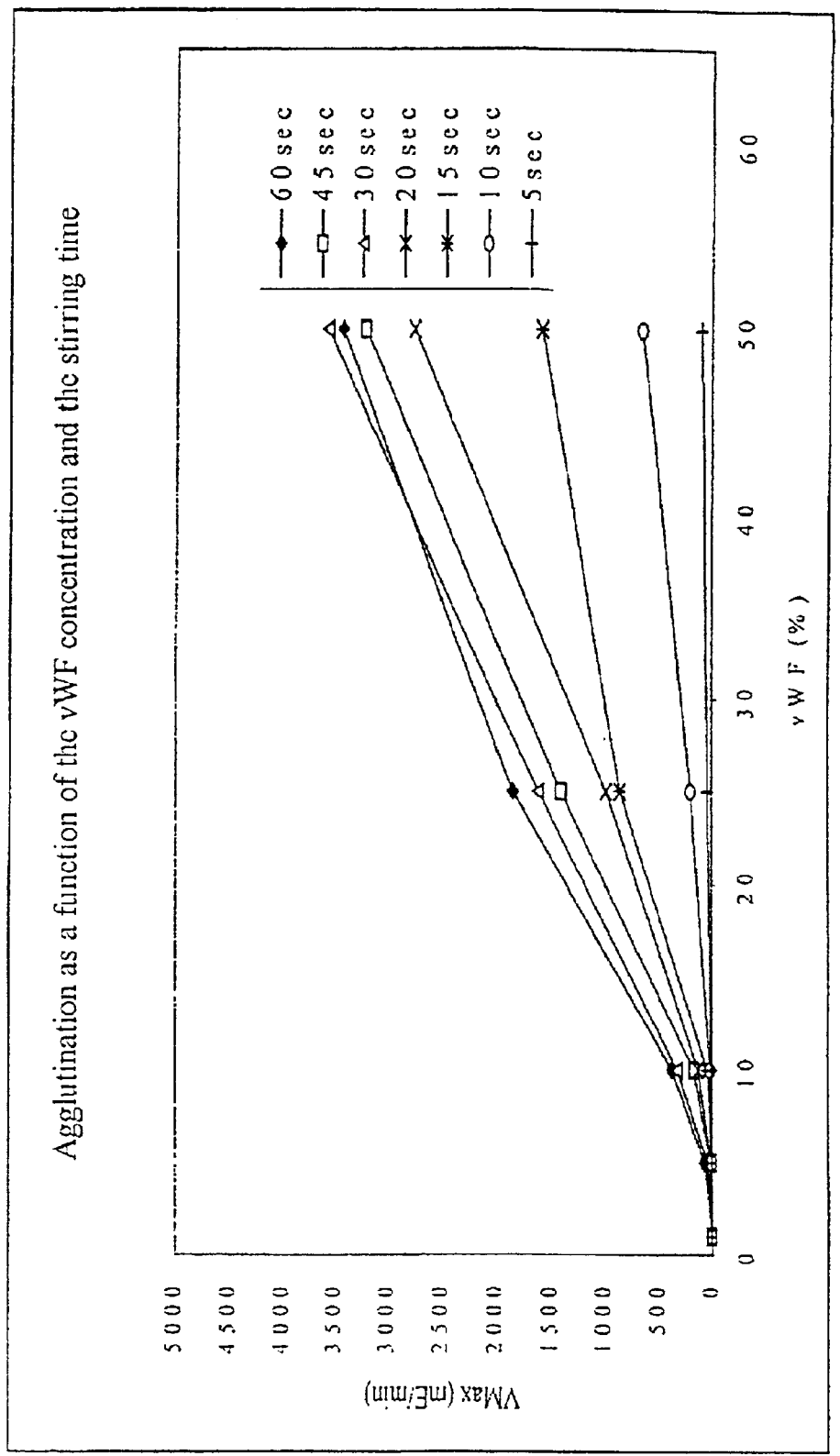

The rate and endpoint of superaggregate formation made possible by pure diffusion are, like the aggregate formation brought about by stirring, dependent on the von Willebrand concentration (FIG. 4, standard human plasma dilutions). This makes it possible for the method of measuring the aggregation also to be such that the reaction mixture is stirred (or mixed in another way) for a short time and only then is the extinction measured. Even very short stirring times of a few seconds can induce superaggregate formation (FIG. 5). Even with these short times there is a concentration dependence in the ristocetin cofactor test, and the precision of the measurements is comparable with those with long stirring times (FIG. 6).

This makes it possible to adapt the ristocetin cofactor test and the platelet aggregation to all automatic analyzers in which adequate and reproducible mixing of the mixture can take place and then the aggregate formation can be measured, for example by turbidimetry or nephelometry. Evaluation is possible both kinetically or by other (for example start and/or end point) methods or else combined methods.

The stability of platelet aggregates can also be established by comparing the aggregation in the method of the invention with an analogous measurement with continuous stirring. With unstable aggregates there is relatively extensive formation of aggregates without continuous stirring compared with the formation of aggregates with continuous stirring. Likewise, the ratio of the formation of aggregates without any stirring at all to that with brief or continuous stirring may be important. It is possible thereby to obtain additional important diagnostic information about the importance under various physiological conditions of the extent of flow processes on activation and aggregate formation and on the stability of platelet aggregates. It is thus possible in the ristocetin cofactor test to investigate the ability of von Willebrand factor or other plasma components to form stable aggregates.

A further possibility is to measure the production and disaggregation of aggregates by alternating phases of stirring and not stirring. This makes it possible to collect important information about the dynamics of such reactions.

The duration of active mixing depends essentially on the nature of the assay and should be 10–60 seconds for example for determining platelet aggregation and 5–60 seconds in the ristocetin cofactor test, and it can generally be said that it may last no longer than 50%, preferably between 1 and 40%, very particularly preferably between 2 and 25%, of the total measurement time.

Aggregate formation in the ristocetin cofactor test takes place with physiologically inactive platelets. It is thus possible also to use in the method of the invention other particles on whose surface receptor molecules mediate, directly or indirectly via ligands, aggregate formation with platelets or with other particles.

The following examples are intended merely to illustrate the invention but not restrict it in any way.

EXAMPLE 1
Determination of Platelet Aggregation with Ristocetin as Agonist (FIG. 1a)

135 µl of platelet-rich plasma were mixed with 15 µl of ristocetin solution (15 mg/ml) and stirred at 600 rpm for 20 or 40 sec. Evaluation took place after stopping the stirrer. For the evaluation, the maximum rate of aggregation (Vmax of the decrease in extinction) after stopping the stirrer was determined (Schreiner, W. et al. Comput. Biol. Med., Vol. 21, No. 6, 435–441, 1991).

EXAMPLE 2
Determination of Platelet Aggregation with Collagen as Agonist (FIG. 1b)

135 µl of platelet-rich plasma were mixed with 15 µl of collagen solution (2000 µg/ml) and stirred at 600 rpm for 20 or 40 sec. Evaluation took place after stopping the stirrer. For the evaluation, the maximum rate of aggregation (Vmax of the decrease in extinction) after stopping the stirrer was determined.

EXAMPLE 3
Determination of Platelet Aggregation with Epinephrine as Agonist (FIG. 1c)

135 µl of platelet-rich plasma were mixed with 15 µl of epinephrine solution (100 µM) and stirred at 600 rpm for 20 or 40 sec. Evaluation took place after stopping the stirrer. For the evaluation, the maximum rate of aggregation (Vmax of the decrease in extinction) after stopping the stirrer was determined.

EXAMPLE 4
Determination of Platelet Aggregation with ADP as Agonist (FIG. 1d)

135 µl of platelet-rich plasma were mixed with 15 µl of ADP solution (200 µM) and stirred at 600 rpm for 20 or 40 sec. Evaluation took place after stopping the stirrer. For the evaluation, the maximum rate of aggregation (Vmax of the decrease in extinction) after stopping the stirrer was determined.

EXAMPLE 5
Determination of Platelet Aggregation with Arachidonic Acid as Agonist (FIG. 1e)

135 µl of platelet-rich plasma were mixed with 15 µl of arachidonic acid solution (5000 µg/ml) and stirred at 600 rpm for 20 or 40 sec. Evaluation took place after stopping the stirrer. For the evaluation, the maximum rate of aggregation (Vmax of the decrease in extinction) after stopping the stirrer was determined.

EXAMPLE 6
Determination of the von Willebrand Ristocetin Cofactor Activity After a Stirring Time of 200 sec. (FIG. 2)

20 µl of plasma were mixed with 20 µl of imidazole buffer and 150 µl of von Willebrand reagent (Dade Behring, Marburg, about 1.2 million formalin-fixed platelets/µl, 1.2 mg/ml ristocetin) and stirred at 600 rpm for 200 seconds. Evaluation took place after stopping the stirrer. For the evaluation, the maximum rate of aggregation (Vmax of the decrease in extinction) after stopping the stirrer was determined.

EXAMPLE 7
Determination of the von Willebrand Ristocetin Cofactor Activity After a Stirring Time of 30 sec. (FIG. 3)

20 µl of plasma were mixed with 20 µl of imidazole buffer and 150 µl of von Willebrand reagent (Dade Behring, Marburg, about 1.2 million formalin-fixed platelets/µl 1.2 mg/ml ristocetin) and stirred at 600 rpm for 30 sec. Evaluation took place after stopping the stirrer. For the evaluation, the maximum rate of aggregation (Vmax of the decrease in extinction) after stopping the stirrer was determined.

EXAMPLE 8
Determination of the von Willebrand Ristocetin Cofactor Activity of Standard Human Plasma Dilutions After a Stirring Time of 30 sec. (FIG. 4)

20 µl of plasma were diluted with imidazole buffer at various levels (100%=undiluted), mixed with a further 20 µl of imidazole buffer and 150 µl of von Willebrand reagent (Dade Behring, Marburg, about 1.2 million formalin-fixed platelets/µl, 1.2 mg/ml ristocetin) and stirred at 600 rpm for 30 seconds. Evaluation took place after stopping the stirrer. For the evaluation, the maximum rate of aggregation (Vmax of the decrease in extinction) after stopping the stirrer was determined.

EXAMPLE 9
Determination of the von Willebrand Ristocetin Cofactor Activity After a Stirring Time of 5–60 sec. (FIG. 5)

40 µl of plasma were mixed with 100 µl of von Willebrand reagent (Dade Behring, Marburg, about 2.4 million formalin-fixed platelets/µl, 2.4 mg/ml of ristocetin) and stirred at 600 rpm for 5, 10, 20, 45 or 60 sec. Evaluation took place after stopping the stirrer. For the evaluation, the maximum rate of aggregation (Vmax of the decrease in extinction) after stopping the stirrer was determined.

EXAMPLE 10
Establishment of Calibration Plots with Standard Human Plasma Dilutions After a Stirring Time of 5–60 sec. (FIG. 6)

40 µl of standard human plasma (about 100% vWF) were diluted with imidazole buffer (50, 25, 10, 5, 1% levels) and mixed with 100 µl of von Willebrand reagent (Dade Behring, Marburg, about 2.4 million formalin-fixed platelets/µl, 2.4 mg/ml ristocetin) and stirred at 600 rpm for 5, 10, 20, 45 or 60 sec. Evaluation took place after stopping the stirrer. For the evaluation, the maximum rate of aggregation (Vmax of the decrease in extinction) after stopping the stirrer was determined.

EXAMPLE 11
Determination of the ADP Concentration Dependence of Platelet Aggregation with and without Continuous Stirring (FIG. 7, Diagram on the Left)

135 µl of platelet-rich plasma were mixed with 15 µl of ADP solution (10 or 25 µM) and stirred at 600 rpm continuously or for 20 seconds. Evaluation took place immediately after the mixing (continuous stirring) or after the stirrer was stopped after 20 seconds. For the evaluation, the maximum rate of aggregation (Vmax of the decrease in extinction) was determined.

EXAMPLE 12
Determination of the Loss of Activity Through Storage of Platelet-Rich Plasma at Room Temperature by Measuring the Aggregation with ADP as Agonist with and without Continuous Stirring (FIG. 7, Diagram on the Right)

135 µl of platelet-rich plasma were mixed with 15 µl of ADP solution (200 µM) and stirred at 600 rpm continuously or for 20 seconds. Evaluation took place immediately after the mixing (continuous stirring) or after the stirrer was stopped after 20 seconds. For the evaluation, the maximum rate of aggregation (Vmax of the decrease in extinction) was determined.

What is claimed is:

1. A method of measuring the macroaggregation of blood platelets, comprising:
   a) obtaining a sample containing blood platelets;
   b) adding at least one activator that induces platelet aggregation to the sample, thereby creating a reaction mixture;
   c) mixing the reaction mixture in a first reaction phase for a time sufficient to induce formation of macroaggregates;
   d) mixing the reaction mixture less vigorously or not at all in a second reaction phase; and
   e) measuring the macroaggregation of the blood platelets in the second reaction phase.

2. The method of claim 1, wherein the mixing is accomplished by stirring, shaking, vibrating, or ultrasound.

3. The method of claim 2, wherein the mixing is performed at a rate between 200 and 2000 rpm.

4. The method of claim 1, wherein the blood platelets are physiologically active blood platelets.

5. The method of claim 1, wherein the sample is chosen from at least one of whole blood, platelet-rich plasma, diluted platelet-rich plasma, and purified platelets.

6. The method of claim 1, wherein measuring the macroaggregation of blood platelets is performed by one of turbidimetric, nephelometric or electromagnetic methods.

7. The method of claim 1, wherein a mixing time is determined by the particular activator or activators used.

8. The method of claim 7, wherein the activators comprise ristocetin, collagen, ADP, epinephrine, or arachidonic acid.

9. A method of measuring the stability of blood platelet macroaggregates comprising:
   a) obtaining a sample containing blood platelets;
   b) adding at least one activator that induces platelet aggregation to the sample, thereby creating a reaction mixture A;
   c) mixing the reaction mixture A in a first reaction phase for a time sufficient to induce formation of macroaggregates;
   d) then mixing reaction mixture A less vigorously or not at all in a second reaction phase and measuring the macroaggregation of blood platelets in the second reaction phase in a first aggregation measurement;
   e) repeating steps a) and b) to generate an analogous second reaction mixture B;
   f) mixing reaction mixture B for a time sufficient to induce formation of macroaggregates, and measuring the macroaggregation of blood platelets in B in a second aggregation measurement wherein the second aggregation measurement is performed while mixing; and
   g) comparing the first aggregation measurement of A to the second aggregation measurement of B.

10. The method of claim 9, wherein the mixing is accomplished by stirring, shaking, vibrating, or ultrasound.

11. The method of claim 10, wherein the mixing is performed at a rate between 200 and 2000 rpm.

12. The method of claim 9, wherein the blood platelets are physiologically active blood platelets.

13. The method of claim 9, wherein the sample is chosen from at least one of whole blood, platelet-rich plasma, diluted platelet-rich plasma, and purified platelets.

14. The method of claim 9, wherein measuring the macroaggregation of blood platelets is performed by one of turbidimetric, nephelometric or electromagnetic methods.

15. The method of claim 9, wherein a mixing time is determined by the particular activator or activators used.

16. The method of claim 15, wherein the activators comprise ristocetin, collagen, ADP, epinephrine, or arachidonic acid.

17. The method of claims 1 or 9, wherein the mixing of any reaction mixture is preceded by an incubation step without mixing.

18. The method of claim 17, wherein there is a sequence of multiple alternating mixing steps and non-mixing incubation steps.

19. The method of claims 1 or 9, wherein an initial aggregation measurement is taken before any reaction mixture is mixed.

20. The method of claims 1 or 9, wherein the macroaggregation aggregation of blood platelets with other particles containing ligands or receptors that facilitate aggregation is measured.

21. The method of claims 1 or 9, wherein the mixing in the second reaction phase is adjusted to a lower intensity than the first reaction phase rather than completely stopped.

22. A method of measuring the macroaggregation of blood platelets, comprising:
   a) obtaining a reagent containing blood platelets;
   b) adding a sample that induces platelet aggregation to the reagent, thereby creating a reaction mixture;
   c) mixing the reaction mixture in a first reaction phase for a time sufficient to induce formation of macroaggregates;
   d) mixing the reaction mixture less vigorously or not at all in a second reaction phase; and
   e) measuring the macroaggregation of the blood platelets in the second reaction phase.

23. The method of claim 22, wherein the mixing is accomplished by stirring, shaking, vibrating, or ultrasound.

24. The method of claim 23, wherein the mixing is performed at a rate between 200 and 2000 rpm.

25. The method of claim 22, wherein the blood platelets are fixed blood platelets.

26. The method of claim 25, wherein platelet macroaggregation is measured using a ristocetin cofactor test.

27. The method of claim 22, wherein measuring the macroaggregation of blood platelets is performed by one of turbid metric, nephelometric or electromagnetic methods.

28. The method of claim 22, wherein the sample is chosen from at least one of whole blood, plasma, platelet-rich plasma, diluted platelet-rich plasma, and purified platelets.

29. A method of measuring the stability of blood platelet macroaggregates, comprising:
   a) obtaining a reagent containing blood platelets:
   b) adding a sample that induces platelet aggregation to the reagent, thereby creating a reaction mixture A;
   c) mixing the reaction mixture A in a first reaction phase for a time sufficient to induce formation of macroaggregates;
   d) then mixing reaction mixture A less vigorously or not at all in a second reaction phase and measuring the macroaggregation of blood platelets in the second reaction phase in a first aggregation measurement;
   e) repeating steps a) and b) to generate an analogous second reaction mixture B;
   f) mixing reaction mixture B for a time sufficient to induce formation of macroaggregates, and measuring the macroaggregation of blood platelets in B in a second aggregation measurement, wherein the second aggregation measurement is performed while mixing; and
   g) comparing the first aggregation measurement of A to the second aggregation measurement of B.

30. The method of claim 29, wherein the mixing is accomplished by stirring, shaking, vibrating, or ultrasound.

31. The method of claim 30, wherein the mixing is performed at a rate between 200 and 2000 rpm.

32. The method of claim wherein the blood platelets are fixed blood platelets.

33. The method of claim 32, wherein platelet macroaggregation is measured using a ristocetin cofactor test.

34. The method of claims 25 or 32, wherein said fixed blood platelets are replaced, in whole or part, by any of other cells, membrane vesicles, or artificial particles containing ligands or receptors that facilitate macroaggregation.

35. The method of claim 29, wherein the sample is chosen from at least one of whole blood, plasma, platelet-rich plasma, diluted platelet-rich plasma, and purified platelets.

36. The method of claim 29, wherein measuring the macroaggregation of blood platelets is performed by one of turbidimetric, nephelometric or electromagnetic methods.

37. The method of claims 22 or 29, wherein the mixing of any reaction mixture is preceded by an incubation step without mixing.

38. The method of claim 37, wherein there is a sequence of multiple alternating mixing steps and non-mixing incubation steps.

39. The method of claims 22 or 29, wherein an initial aggregation measurement is taken any reaction mixture is mixed.

40. The method of claims 22 or 29, wherein the macroaggregation of blood platelets with other particles containing ligands or receptors that facilitate aggregation is measured.

41. The method of claims 22 or 29, wherein the mixing in the second reaction phase is adjusted to a lower intensity than the first reaction phase rather than completely stopped.

* * * * *